(12) United States Patent
Suzuki et al.

(10) Patent No.: US 9,733,384 B2
(45) Date of Patent: Aug. 15, 2017

(54) PACKAGE INSPECTION SYSTEM

(71) Applicant: System Square Inc., Nagaoka-shi, Niigata (JP)

(72) Inventors: Atsushi Suzuki, Nagaoka (JP); Noriaki Ikeda, Nagaoka (JP)

(73) Assignee: System Square Inc., Niigata (JP)

( * ) Notice: Subject to any disclaimer, the term of this patent is extended or adjusted under 35 U.S.C. 154(b) by 0 days.

(21) Appl. No.: 14/418,895

(22) PCT Filed: Oct. 3, 2013

(86) PCT No.: PCT/JP2013/076984
§ 371 (c)(1),
(2) Date: Jan. 30, 2015

(87) PCT Pub. No.: WO2015/049765
PCT Pub. Date: Apr. 9, 2015

(65) Prior Publication Data
US 2016/0033404 A1     Feb. 4, 2016

(51) Int. Cl.
*G01N 21/59* (2006.01)
*G01N 21/3581* (2014.01)
(Continued)

(52) U.S. Cl.
CPC ....... *G01V 5/0016* (2013.01); *G01N 21/3581* (2013.01); *G01V 8/10* (2013.01); *G01V 11/00* (2013.01)

(58) Field of Classification Search
CPC ...... G01N 21/3581; G01N 21/59; H04N 5/32; G01V 11/00; G01V 5/0016
See application file for complete search history.

(56) References Cited

U.S. PATENT DOCUMENTS 5,901,198 A * 5/1999 Crawford ............... G01V 5/005
378/15
6,324,253 B1 * 11/2001 Yuyama ................. G01N 23/04
209/589
(Continued)

FOREIGN PATENT DOCUMENTS

EP    1 739 412 A1    1/2007
JP    U1-S58-17544    7/1983
(Continued)

OTHER PUBLICATIONS

JP Office Action issued Nov. 4, 2014 in related case JP 2014-540243, pp. 1-8.
(Continued)

*Primary Examiner* — David Porta
*Assistant Examiner* — Faye Boosalis
(74) *Attorney, Agent, or Firm* — Brinks, Gilson & Lione (57) ABSTRACT

A package inspection system is provided, where an electromagnetic-wave detection part is hardly affected by illumination light for optical detection. Below a gap 6c of a conveyor mechanism 6 for conveying a package, provided are an X-ray sensor 13 for detecting X rays transmitted through the package and an illumination part 16 for applying illumination light to the gap 6c. The X-ray sensor 13 and the illumination part 16 are separated from each other by a partition 42. A light-shielding member 43 is placed in the path of X-ray incidence to the X-ray sensor 13. The light-shielding member 43 is formed of a material that allows passage of the X rays but does not allow passage of the illumination light and is hardly deteriorated by irradiation of the X rays, e.g., a carbon sheet.

9 Claims, 9 Drawing Sheets

(51) Int. Cl.
  *G01V 5/00*    (2006.01)
  *G01V 8/10*    (2006.01)
  *G01V 11/00*   (2006.01)

(56) References Cited

U.S. PATENT DOCUMENTS

| | | |
|---|---|---|
| 2006/0056586 A1 | 3/2006 | Uetake et al. |
| 2006/0185087 A1* | 8/2006 | Coppens .............. A61B 6/0442 5/601 |
| 2012/0327227 A1 | 12/2012 | Ikeda et al. |

FOREIGN PATENT DOCUMENTS

| | | |
|---|---|---|
| JP | A-H02-52246 | 2/1990 |
| JP | A-H09-127017 | 5/1997 |
| JP | A-2000-135268 | 5/2000 |
| JP | U-3175930 | 6/2001 |
| JP | A-2002-168803 | 6/2002 |
| JP | 2006-208098 A | 8/2006 |
| JP | A-2006-208098 | 8/2006 |
| JP | A-2009-42172 | 2/2009 |
| JP | A-2011-128046 | 6/2011 |
| JP | A-2013-7597 | 1/2013 |

OTHER PUBLICATIONS

Extended European Search Report dated Apr. 26, 2017 for European Application No. 13889357.3, 7 pages.

* cited by examiner

PACKAGE INSPECTION SYSTEM

This application is a filing under 35 U.S.C. § 371 of International Patent Application PCT/JP2013/076984, entitled "Package Inspection System", filed on Oct. 3, 2013, the content of which is incorporated herein by reference in its entirety.

TECHNICAL FIELD

The present invention relates to a package inspection system capable of inspecting a package with both an electromagnetic-wave detector for detecting X rays or terahertz waves and an optical detector.

RELATED ART

In the process of manufacturing a package containing foods, an inspection system utilizing X rays has been used. Such an inspection system has been mainly used to examine whether or not any foreign body other than foods are present in the package.

An inspection system disclosed in Patent Literature 1 has an X-ray foreign body detection device equipped with a conveyor belt for conveying an object to be inspected. With the conveyor belt between, the X-ray foreign body detection device has an X-ray source at the upper side and an X-ray line sensor at the lower side. The X-ray foreign body detection device also has a CCD camera for taking an external optical image of an object to be inspected.

This inspection system is configured such that specific identification information such as serial number put on an object to be inspected is obtained by taking the external optical image and a single synthesis inspection image obtained by combining the result of the X-ray inspection with the specific identification information is recorded on an accumulation/record means.

PATENT LITERATURE

Patent Literature 1: Japanese Unexamined Patent Application Publication No. 2006-208098

SUMMARY OF INVENTION

Technical Problem

In the inspection system having both the X-ray line sensor and the CCD camera, as in Patent Literature 1, since the external optical image is to be taken by the CCD camera, an object to be inspected has to be examined in a relatively bright place where it can be observed by the CCD camera. This increases the likelihood that light other than X rays will enter the X-ray line sensor. If too much light other than X rays is applied to the X-ray line sensor, SNR at the time of detecting X rays having passed through an object to be inspected will be worsened to deteriorate the inspection accuracy for inspection of whether or not any foreign body is present in an package.

The present invention is to solve the above-mentioned problem in the prior art and has an object to provide a package inspection system which includes an optical inspection device but makes it difficult for illumination light to enter an electromagnetic-wave detector for detecting X rays or terahertz waves.

Solution to Problem

The present invention is characterized by comprising: a conveyor mechanism for conveying a package having a content in a wrapping; an irradiation part for irradiating the package with an X ray or a terahertz wave; an electromagnetic-wave detection part for detecting the X ray or terahertz wave transmitted through the package; an illumination part for illuminating the package; and an optical detection part for taking an optical image of the package, a partition being provided between the electromagnetic-wave detection part and the illumination part, the partition having a light-shielding member configured to allow passage of the X ray or terahertz wave but block or reduce the light emitted from the illumination part, at least in a path through which the X ray or terahertz wave enter the electromagnetic-wave detection part.

In the package inspection system according to the present invention, since the light from the illumination part can be blocked by the partition, the light emitted from the illumination part can be prevented from entering the electromagnetic-wave detection part. Moreover, since the light-shielding member configured to allow passage of the X ray or terahertz wave but block or reduce the light emitted from the illumination part is placed in the incident path to the electromagnetic-wave detection part, the electromagnetic-wave detection part can detect the X ray or terahertz wave such that a sufficient detection output can be generated without being affected by the light from the illumination part.

In the package inspection system according to the present invention, the light emitted from the illumination part and having passed the package can be detected by the optical detection part. Therefore, the outline of the package can be obtained as an image with high accuracy. If the wrapping of the package is formed of a light transmissive material, the inspection of the content or the determination of whether or not the content is caught in a seal can be performed by detecting the transmitted light with the optical detection part, without using the X ray or terahertz wave.

In the present invention, the irradiation part and the optical detection part may be provided at one side of a conveyance path of the package, and the illumination part and the electromagnetic-wave detection part may be provided at the other side thereof.

In the present invention, the illumination part may be enclosed by the partition, the electromagnetic-wave detection part may be provided outside the partition, and the partition may be provided with the light-shielding member at a position facing the electromagnetic-wave detection part. Alternatively, the electromagnetic-wave detection part may be enclosed by the partition, the illumination part may be provided outside the partition, and the partition may be provided with the light-shielding member at a position facing the electromagnetic-wave detection part.

In the present invention, the light-shielding member may contain carbon, and for example, the light-shielding member may be a carbon sheet containing carbon fibers and a binder resin. Alternatively, the light-shielding member may be formed of a PEEK (polyether ether ketone) resin.

The light-shielding member formed of such materials has a good X-ray or terahertz-wave transmittance and is hardly deteriorated by the X ray or terahertz wave.

In the present invention, a cover member configured to allow passage of the X ray or terahertz wave and the light emitted from the illumination part may be provided between a conveyance path of the package and the electromagnetic-wave detection part and the illumination part.

For example, the cover member may be formed of a thermoplastic polyetherimide resin.

In the present invention, the conveyor mechanism may have a gap through which the light emitted from the illumination part and the X ray or terahertz wave is allowed to pass.

With this configuration, a scratch on a conveyor belt or a foreign body attached to the conveyor belt can be prevented from being detected by the electromagnetic-wave detection part or the optical detection part.

Advantageous Effects of Invention

In the present invention, since the light from the illumination part can be blocked by the partition in a package inspection zone, the light emitted from the illumination part can be prevented from entering the electromagnetic-wave detection part. Moreover, since the light-shielding member configured to allow passage of the X rays or terahertz waves but block or reduce the light emitted from the illumination part is placed in the incident path to the electromagnetic-wave detection part, the electromagnetic-wave detection part can detect the X rays or terahertz waves such that a sufficient detection output can be generated without being affected by the light from the illumination part.

Therefore, the amount of light from the illumination part can be increased to let the optical detection part detect the light having passed the package while preventing the light from being detected by the electromagnetic-wave detection part.

DESCRIPTION OF EMBODIMENTS

Figure 1:
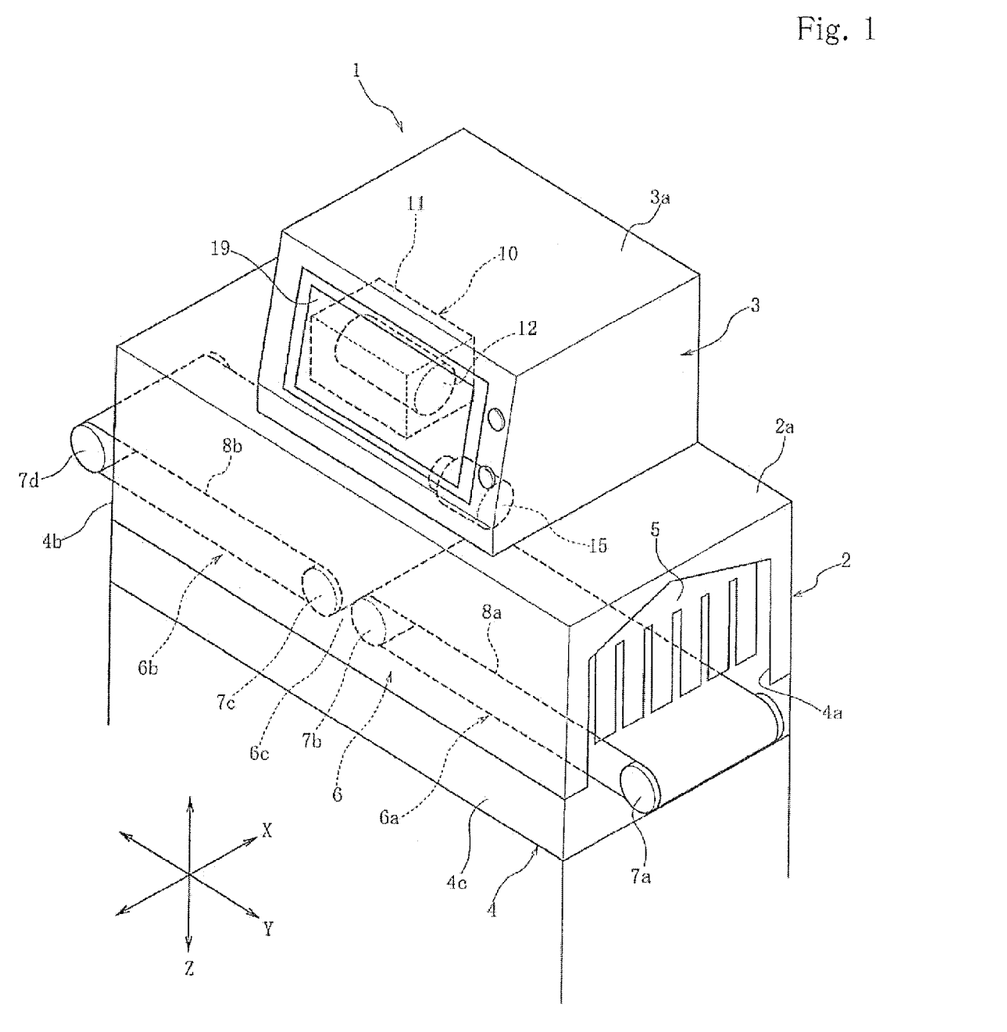
FIG. 1 A perspective view showing the appearance of a package inspection system according to a first embodiment of the present invention.

As shown in FIG. 1, an inspection system 1 according to a first embodiment of the present invention has a package conveyance zone 2, an overlying upper housing 3, and a lower housing 4 placed below the package conveyance zone 2.

The package conveyance zone 2 is formed inside an intermediate enclosure 2a. The intermediate enclosure 2a has an inlet 4a at one end and an outlet 4b at the other opposite end. Each of the inlet 4a and the outlet 4b is provided with an X-ray shielding sheet 5, so that the package conveyance zone 2 inside the intermediate enclosure 2a becomes an electromagnetic-wave shielding zone (X-ray shielding zone).

Figure 2:
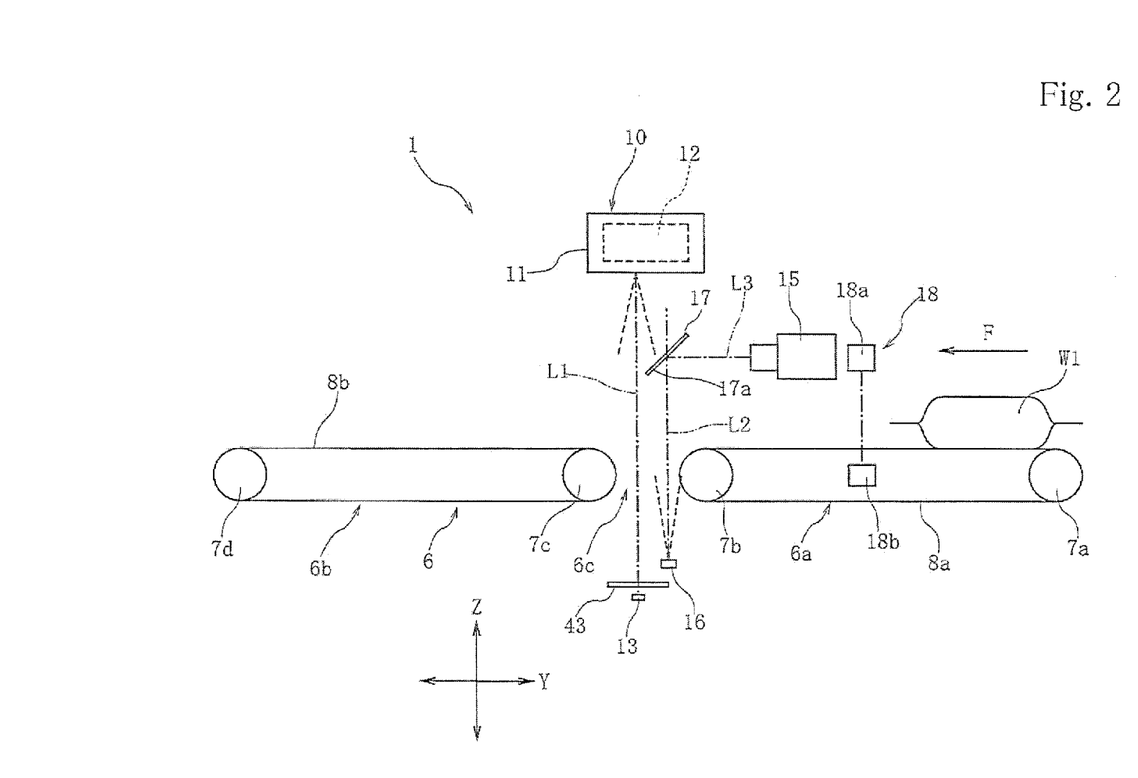
FIG. 2 A front view showing the internal construction of the package inspection system according to the first embodiment.

A conveyor mechanism 6 is provided in the package conveyance zone 2. As shown in FIGS. 1 and 2, the conveyor mechanism 6 is separated into an upstream conveyor mechanism 6a and a downstream conveyor mechanism 6b, forming a gap 6c at which a space is left between the upstream conveyor mechanism 6a and the downstream conveyor mechanism 6b in the moving direction.

The upstream conveyor mechanism 6a has an upstream roller 7a and a downstream roller 7b with a conveyor belt 8a stretched between the rollers 7a and 7b. One of the upstream roller 7a or the downstream roller 7b is a driving roller and the other is a driven roller. The downstream conveyor mechanism 6b has an upstream roller 7c and a downstream roller 7d with a conveyor belt 8b stretched between the rollers 7c and 7d. One of the upstream roller 7c or the downstream roller 7d is a driving roller and the other is a driven roller.

The upstream conveyor belt 8a is a light transmissive belt. For example, it is a transparent or semi-transparent belt made of a synthetic resin or a rubber belt having a large number of apertures regularly arranged therein. The downstream conveyor belt 8b may be a light transmissive one or a light non-transmissive one.

The upstream conveyor belt 8a and the downstream conveyor belt 8b travel around at the same speed. With the upstream conveyor belt 8a travelling around, a package W1 put on an upstream end of the upstream conveyor belt 8a is brought into the package conveyance zone (electromagnetic-wave shielding zone) 2 through the inlet 4a and conveyed at a constant speed leftward in the drawing (in the F direction). Then, after passing the gap 6c, it is received by the downstream conveyor belt 8b and brought out of the outlet 4b with the conveyor belt 8b travelling around.

In FIG. 1, the moving direction (F direction) of the package W1 is Y direction, and the direction perpendicular to the moving direction (F direction) is X direction. On the other hand, the direction vertical to the moving direction (F direction) is Z direction.

As shown in FIG. 1, the upper housing 3 has an upper enclosure 3a, and an X-ray generator 10 is housed in the upper enclosure 3a. The X-ray generator 10 has an X-ray tube housed in a sealed container 11. The lower housing 4 has a lower enclosure 4c, and an X-ray sensor 13 shown in FIG. 2 is placed therein.

In the present embodiment, the X-ray tube 12 is used as an electromagnetic-wave irradiation part, and the X-ray sensor 13 is used as an electromagnetic-wave detection part. However, the electromagnetic-wave irradiation part may irradiate terahertz waves, and the electromagnetic-wave detection part may be composed of elements capable of detecting terahertz waves transmitted through the package W1.

In the upper housing 3, an optical sensor 15 is provided as an optical detection part; in the lower housing 4, an illumination part 16 is provided. The optical sensor 15 is a line sensor having a plurality of light detection elements arranged linearly in the X direction perpendicular to the moving direction of the package W1 so as to form a light detection line. The optical sensor 15 may have either a single or a plurality of light detection lines extending in the X direction.

Figure 3:
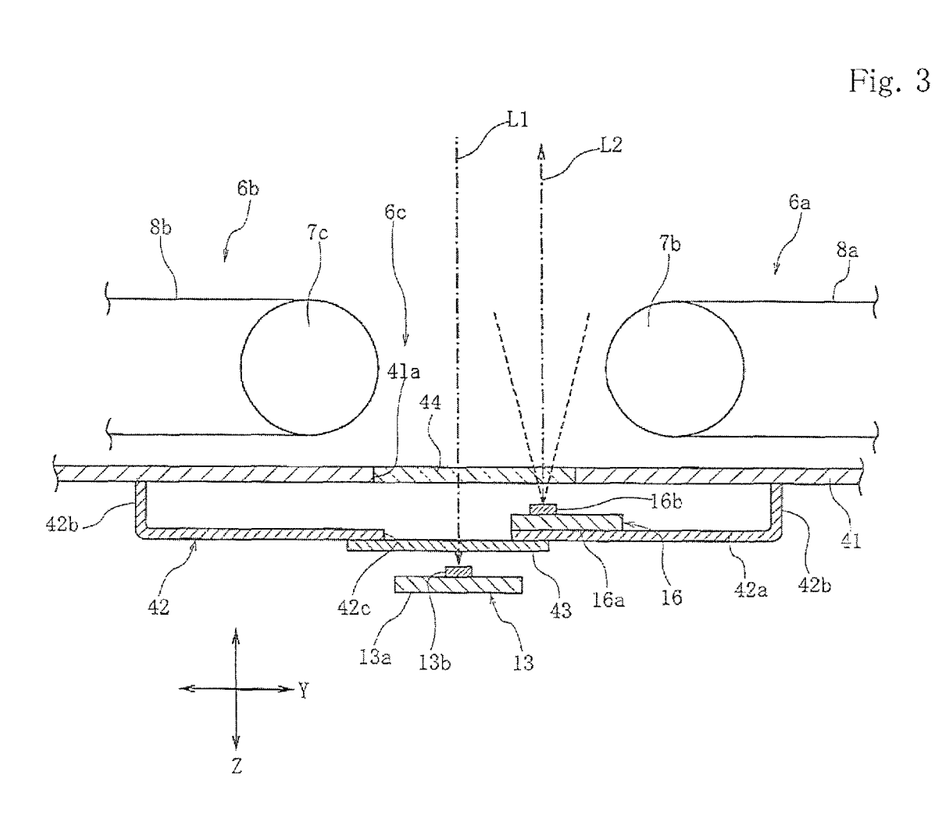
FIG. 3 A sectional view showing the arrangement of an illumination part and an electromagnetic-wave detection part.

As shown in FIG. 3 on an enlarge scale, a floor plate 41 formed of a stainless steel is placed below the gap 6c of the conveyor mechanism 6 in parallel to the X-Y plane. The floor plate 41 forms a part of a ceiling of the lower enclosure 4c. The X-ray sensor 13 and the illumination part 16 are housed in the lower housing 4 lying below the floor plate 41.

Figure 4:
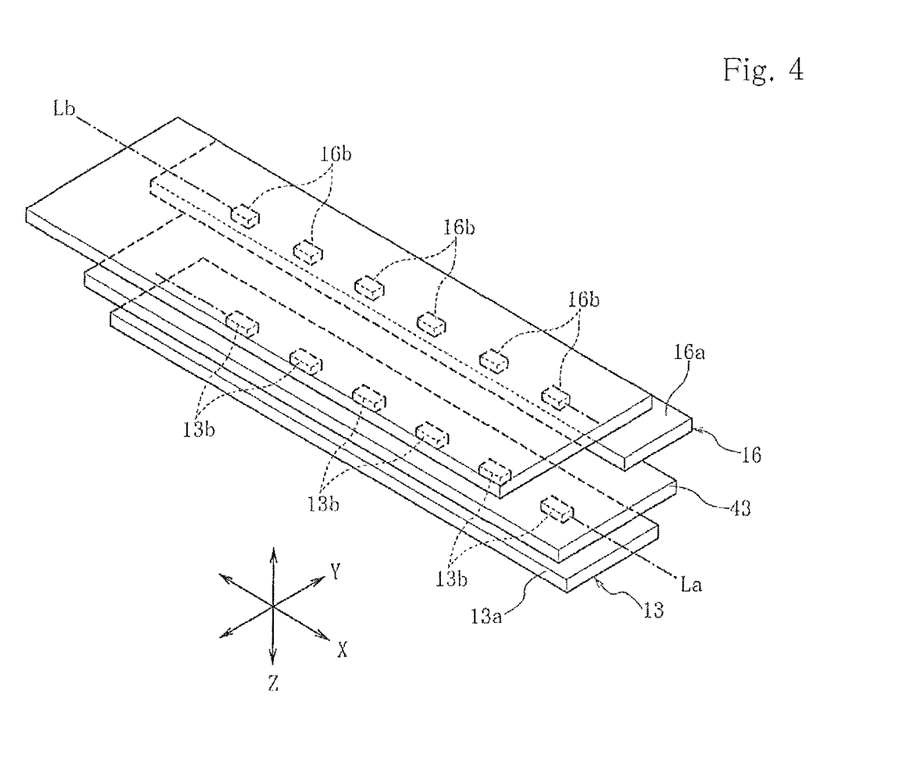
FIG. 4 A perspective view showing the arrangement of an illumination part and an electromagnetic-wave detection part.

The X-ray sensor 13 is a line sensor having a plurality of X-ray detection elements 13b mounted on a sensor substrate 13a, as shown in FIG. 4. The plurality of X-ray detection elements 13b are arranged in the X direction perpendicular to the moving direction of the package W1 so as to form an X-ray detection line La. The X-ray detection element 13b is a photodiode chip. The X-ray sensor 13 has a single X-ray detection line La extending in the X direction but may have a plurality of the lines.

The illumination part 16 is a line illumination device having a plurality of light-emitting elements 16b mounted on a illumination substrate 16a, as shown in FIG. 4. The plurality of light-emitting elements 16b are arranged in the X direction perpendicular to the moving direction of the package W1 so as to form an illumination line Lb. The illumination line Lb is a single line but may be composed of a plurality of lines.

The light-emitting element 16b is a light-emitting diode (LED) which emits near infrared light or light having a blue wavelength.

As shown in FIG. 3, a partition 42 formed of a stainless steel is placed beneath the floor plate 41. The partition 42 is a single bent member having a support plate 42a and a side plate 42b, and the illumination substrate 16a of the illumination part 16 is fixed on the support plate 42a. The side plate 42b is joined to the lower surface of the floor plate 41 without leaving any space. The illumination part 16 is located within the region defined by the partition 42, while the X-ray sensor 13 is located outside the partition 42 and below the support plate 42a.

The support plate 42a of the partition 42 has a detection window 42c above the X-ray sensor 13, and this detection window 42c is closed with a light-shielding member 43. The light-shielding member 43 is a plate or sheet and formed of a material that allows passage of the X rays but is capable of blocking the illumination light emitted from the illumination part 16 or reducing the transmittance of the illumination light. In order to endure long-term use, particularly, it is preferably formed of a material that is hardly deteriorated by X rays.

As the material that is hardly deteriorated by X rays, it is preferable to use a sheet containing carbon. For example, it may be a carbon sheet having carbon fibers fixed with a binder resin, a carbon sheet having a woven or nonwoven fabric of carbon fibers reinforced with a binder resin, or a carbon sheet containing a carbon material such as carbon black in a resin. Since the carbon can convert the energy of X rays into heat and dissipate the heat, it can withstand long-term irradiation of X rays.

It is also possible to use a PEEK resin (polyether ether ketone resin) as the material that is hardly deteriorated by X rays. Since the PEEK resin is a thermoplastic resin that can be easily formed into a sheet or plate and is super heat-resistant, it can withstand long-term irradiation of X rays.

As shown in FIG. 3, the floor plate 41 has an opening 41a, and the X-ray detection elements 13b of the X-ray sensor 13 and the light-emitting elements 16b of the illumination part 16 are located beneath the opening 41a. The opening 41a is closed with a cover member 44. The cover member 44 is formed of a material that allows passage of both the light emitted from the illumination part 16 and the X rays but is hardly deteriorated by long-term irradiation of X rays.

For example, the cover member 44 is formed of a ULTEM resin (registered trademark) that is an amorphous thermoplastic polyetherimide resin. With the cover member 44, dirt or dust can be prevented from falling on the region where the illumination part 16 is located or the region where the light-shielding member 43 is located.

In FIG. 2, the centerline of the X-ray detection area in which X rays can be detected by the X-ray sensor 13 (X-ray detection image-taking line) is indicated by L1. The X-ray detection image-taking line (electromagnetic-wave detection image-taking line) L1 is a line joining the center of the X-ray generator 10 and the center of the X-ray sensor 13. Moreover, the X-ray detection image-taking line represents a detection plane parallel to the X-Z plane rising vertically from the X-ray detection line of the X-ray sensor 13 being a line sensor, and therefore can be restated as X-ray detection image-taking plane. The X-ray detection image-taking line L1 of the X-ray sensor 13 passes through the gap 6c of the conveyor mechanism 6 and extends in the Z direction perpendicular to the Y direction being the moving direction of the package W1.

In FIG. 2, the centerline of the light detection area in which light can be detected by the optical sensor 15 (light detection image-taking line) is indicated by L2 and L3. The light detection image-taking line L2 and L3 is a line joining the center of the optical sensor 15 and the center of the illumination part 16. Moreover, the light detection image-taking line L2 and L3 represents a detection plane extending from the light detection line of the optical sensor 15 with a depth in the X direction, and therefore can be restated as light detection image-taking plane.

As shown in FIG. 2, a reflection member 17 is provided above the conveyor mechanism 6. The reflection surface 17a of the reflection member 17 is inclined 45 degrees with respect to the X-Z plane. The light detection image-taking line L3 of the optical sensor 15, which extends parallel to the Y direction, is bent downward by the reflection surface 17a of the reflection member 17 and becomes the light detection image-taking line L2. That is, the illumination light emitted from the illumination part 16 passes the package W1 passing above the gap 6c and is reflected by the reflection surface 17a and received by the optical sensor 15.

The X-ray sensor 13 and the illumination part 16 are closely arranged beneath the conveyor mechanism 6, and the X-ray detection image-taking line L1 and the light detection image-taking line L2 are arranged parallel to each other without coinciding in the gap 6c of the conveyor mechanism 6.

In the inspection system 1 shown in FIG. 2, since the X-ray detection image-taking line L1 and the light detection image-taking line L2 run through the same gap 6c, optical image data due to detection by the optical sensor 15 can be obtained at the same conditions as image data that can be obtained by applying X rays to the package W1 passing the gap 6c.

Moreover, since the reflection member 17 is placed so as not to cross the X-ray detection image-taking line L1, the reflection member 17 can be certainly prevented from being deteriorated by the irradiation of the X rays.

As shown in FIG. 2, a position sensor 18 is provided in the upstream conveyor mechanism 6a. The position sensor 18 is an optical sensor composed of a light-emitting part 18a and a light-receiving part 18b facing each other. With the conveyance path of the package W1 between, the light-emitting part 18a is placed at the upper or lower side thereof, and the light-receiving part 18b faces it at the other side thereof. It should be noted that if the upstream conveyor belt 8a is not a light transmissive one, the light-emitting part 18a and the light-receiving part 18b may face each other in the X direction so as to detect the package W lying on the conveyance surface of the conveyor belt 8a.

As shown in FIG. 1, a display unit 19 and a control panel are provided at the front part of the upper enclosure 3a constituting the upper housing 3. The display unit 19 may be composed of a display panel such as color liquid crystal panel and its driving circuit. Various types of operation buttons are arranged on the control panel.

Figure 8:
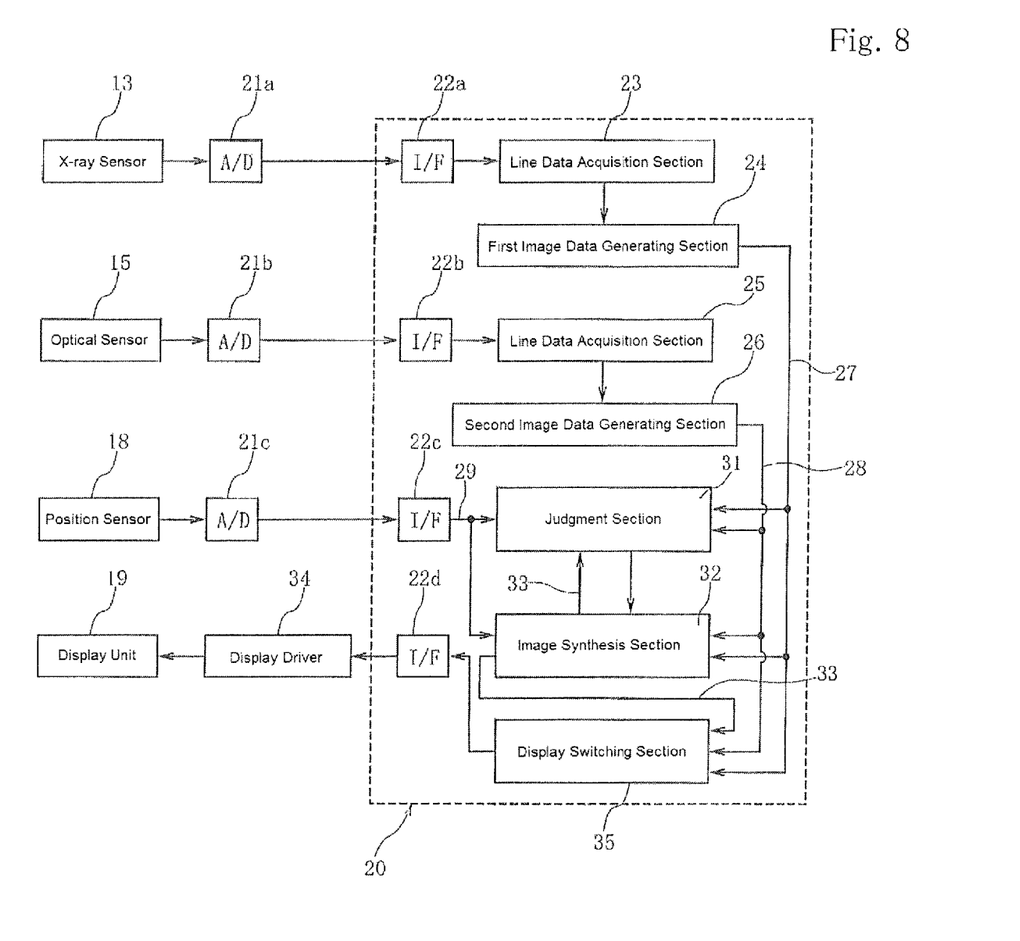
FIG. 8 A circuit block diagram of an inspection system according to the present invention.

FIG. 8 shows a circuit block diagram illustrating the outline of an electronic circuit provided in the inspection system 1.

A controller 20 may be composed of a CPU and a memory; the blocks inside the controller 20 shown in FIG. 8 can be configured by executing software installed in the CPU.

Detection output from the X-ray sensor 13 can be converted into digital signals at an A/D converter 21a and sent to a line data acquisition section 23 of the controller 20 via an input interface 22a. At the line data acquisition section 23, density data detected at the X-ray detection line of the X-ray sensor 13 can be acquired on a line-by-line basis. The density data for each line acquired at the line data acquisition section 23 can be sent to and accumulated at a first image data generating section 24, thereby generating a first image data 27 composed of display-sized density data.

Detection output from the optical sensor 15 can be converted into digital signals at an A/D converter 21b and sent to a line data acquisition section 25 of the controller 20 via an input interface 22b. At the line data acquisition section 25, density data detected at the light detection line of the optical sensor 15 can be acquired on a line-by-line basis. The density data for each line acquired at the line data acquisition section 25 can be sent to and accumulated at a second image data generating section 26, thereby generating a second image data 28 composed of display-sized density data.

As shown in FIG. 8, the first image data 27 generated at the first image data generating section 24 as a density image from the X-ray detection output can be sent to a judgment section 31, an image synthesis section 32 and a display switching section 35. The second image data 28 generated at the second image data generating section 26 as a density image from the light detection output can also be sent to the judgment section 31, the image synthesis section 32 and the display switching section 35. The judgment section 31 and the image synthesis section 32 allow data interchanges between each other.

Detection output from the position sensor 18 can be converted into digital signals at an A/D converter 21c and sent to the judgment section 31 and the image synthesis section 32 as timing signals 29 via an input interface 22c.

At the image synthesis section 32, the first image data 27 and the second image data 28 are combined together. Combined image data 33 obtained by combining two types of image data can be sent to the display switching section 35. The combined image data 33 can also be sent to the judgment section 31.

The display switching section 35 can be operable to switch by operating one of the operation buttons on the display panel. The combined image data 33 or the first image data 27 or the second image data 28 can be chosen by the display switching section 35 and sent to a display driver 34 via an output interface 22d. The display unit 19 can be driven by the display driver 34 so that the screen of the display panel can display an image based on the combined image data 33. Alternatively, the screen can display an image based on the first image data 27 or an image based on the second image data 28.

The inspection procedure of the package W1 using the inspection system 1 will be described hereinbelow.

Figure 9A:
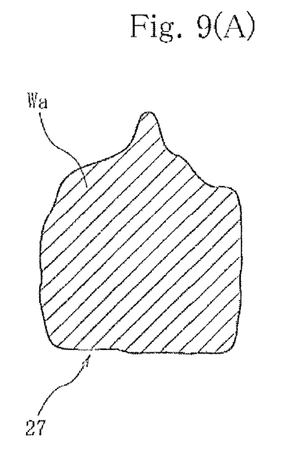
FIG. 9 Illustrations of image data acquired by an inspection system according to the present invention.
Figure 9B:
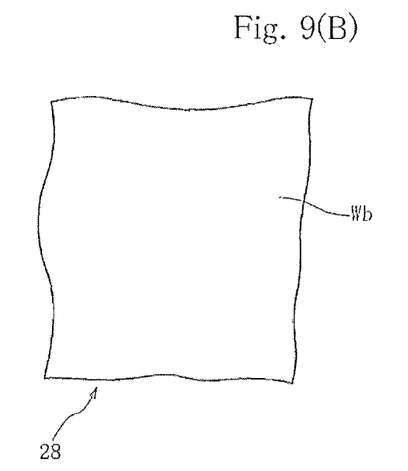
Figure 9C:
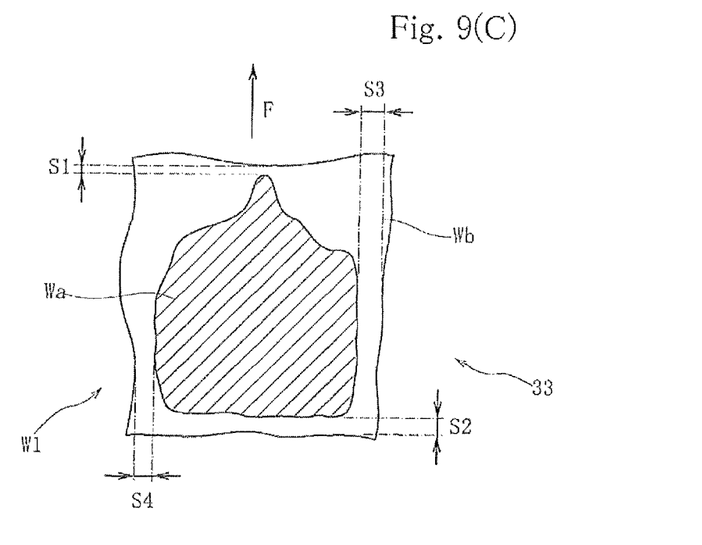

The package W1 shown in FIG. 9(C) is formed by enclosing a content Wa in a wrapping Wb. In the inspection system 1, as shown in FIG. 2, the package W1 is conveyed in the F direction by the conveyor belt 8a of the upstream conveyor mechanism 6a, passed across the gap 6c and received by the conveyor belt 8b of the downstream conveyor mechanism 6b.

The wrapping Wb of the package W1 is a bag that is formed of a synthetic resin film that is subjected to printing and therefore cannot be optically seen through, a bag that is formed of a thin metal foil such as aluminum foil and therefore cannot be optically seen through or a bag that is formed of a laminate of a metal foil and a synthetic resin film and therefore cannot be optically seen through. Alternatively, it may be a bag enclosing a tray formed of a thin synthetic resin material.

The content Wa of the package W1 may be snack, processed food for retort pouch, processed meat or fish or fresh food.

When the package W1 being conveyed by the conveyor mechanism 6 passes the position sensor 18, the timing signal 29 obtained from the detection output is sent to the judgment section 31 and the image synthesis section 32 shown in FIG. 8.

When the package W1 passes the gap 6c of the conveyor mechanism 6, the package W1 is irradiated with the X rays emitted from the X-ray generator 10, so that the X rays transmitted through the package W1 can be detected by the X-ray sensor 13 after passing through the cover member 44 and the light-shielding member 43 shown in FIG. 3.

The detection output from the X-ray sensor 13 is sent to the line data acquisition section 23 of the controller 20 shown in FIG. 8, and the line image data are accumulated at the first image data generating section 24 to generate the first image data 27. Since the wrapping Wb of the package W1 is formed of a thin packaging material, a large amount of X rays can be transmitted. On the other hand, the thickness of the content reduces the amount of X-ray transmission. The first image data 27 show the density contrast of the detected amount of X rays; the first data image includes image data showing the outline of the content Wa, as illustrated in FIG. 9(A), but does not substantially include image data showing the outline of the wrapping Wb.

Also, the illumination light is applied to the gap 6c from the illumination part 16. The illumination light passes through the cover member 44, so that the package W1 passing the gap 6c can be illuminated from below. The illumination light passes the package W1, and the transmitted light is reflected by the reflection member 17 and detected by the optical sensor 15.

The detection output from the optical sensor 15 is sent to the line data acquisition section 25 of the controller 20, and the line image data are accumulated at the second image data generating section 26 to generate the second image data 28. Since the wrapping Wb of the package W1 is formed of a light non-transmissive packaging material, the second image data 28 include an image showing the outline of the wrapping Wb, as illustrated in FIG. 9(B), but do not include an image showing the outline of the content Wa.

When the package W1 being conveyed in the F direction by the conveyor mechanism 6 is detected by the position sensor 18, the timing signal 29 teaching the detection timing is sent to the judgment section 31 and the image synthesis section 32.

The controller 20 has a counter which begins to measure the passage of time from the moment of receiving the timing signal 29 due to detection of the package W1. Alternatively, it may begin to count the number of lines of the line image data obtained from the X-ray sensor 13 and the line image data obtained from the optical sensor 15 from the moment of receiving the timing signal.

At the judgment section 31 and the image synthesis section 32, the first image data 27 and the second image data 28 are acquired at the same timing based on the timing signal. In other words, the image data are acquired such that the image data of the content Wa included in the first image data 27 coincide in relative position with the image data of the wrapping Wb included in the second image data 28.

It should be noted that when the package W1 on the conveyor mechanism 6 is being conveyed with its side edge inclined with respect to the X direction, the first image data 27 and the second image data 28 can be amended to correct the inclination within the X-Y coordinate plane such that the side of the package W1 in the image extends along the X direction.

As shown in FIG. 3, the illumination part 16 and the X-ray sensor 13 are separated from each other by the partition 42 and the light-shielding member 43, so that the illumination light emitted from the illumination part 16 is hardly detected by the X-ray sensor 13. Therefore, the illumination light can be continuously emitted from the illumination part 16 while the X rays transmitted through the package W1 are being detected by the X-ray sensor 13.

The light passing the package W1 can be continuously detected by the optical sensor 15 with the illumination light emitted continuously during the image detection by the X-ray sensor 13, which increases the amount of data: the first image data 27 acquired by the X-ray sensor 13 and the second image data 28 acquired by the optical sensor 15 as the package W1 passes the gap 6c. It is also possible to increase the conveyance velocity of the package W1 by the conveyor mechanism 6.

FIG. 9(C) shows a combined image data 33 produced at the image synthesis section 32. The combined image data 33 are produced by superposing the first image data 27 and the second image data 28 to occupy the same position based on the timing signal from the position sensor 18. In the combined image data 33, the positional relationship between the image of the content Wa and the image of the wrapping Wb is accurately the same as in the moving package W1. After the selection by the display switching section 35, the combined image data 33 shown in FIG. 9(C) are sent to the display driver 34 and displayed on the display screen of the display unit 19.

At the judgment section 31 of the controller 20, the data about the relative position of the image data of the content Wa and the image data of the wrapping Wb are calculated based on the combined image data 33 produced at the image synthesis section 32. In the example shown in FIG. 9(C), calculated are the minimum distance S1 between the front edge of the wrapping Wb and the content Wa, the minimum distance S2 between the rear edge of the wrapping Wb and the content Wa, the minimum distance S3 between the right edge of the wrapping Wb and the content Wa, and the minimum distance S4 between the left edge of the wrapping Wb and the content Wa.

Whether or not a part of the content Wa is caught in a seal of the wrapping Wb can be determined by obtaining the minimum distances S1, S2, S3 and S4. In the example shown in FIG. 9(C), it is determined that since the minimum distance S1 between the front edge of the wrapping Wb and the content Wa is smaller than a predetermined threshold, there is a high possibility that at the front edge of the wrapping Wb, a part of the content Wa is caught in a seal in which the packaging materials are bonded together, causing a seal failure.

At the judgment section 31 of the controller 20, the relative position of the content Wa and the wrapping Wb may also be determined such that the parameters S1, S2, S3 and S4 are calculated by comparing two types of image data 27 and 28 merely on data without superposing and combining the first image data 27 and the second image data 28.

For example, at the judgment section 31, a first group of coordinate points composed of a plurality of coordinate points indicating the outline of the content Wa included in the first image data 27 are determined on the X-Y coordinates based on the timing signal from the position sensor 18; a second group of coordinate points composed of a plurality of coordinate points indicating the outline of the wrapping Wb included in the second image data 28 are also determined on the X-Y coordinates based on the timing signal. Then, the parameters S1, S2, S3 and S4 are calculated by comparing the first group of coordinate points and the second group of coordinate points.

If a foreign body other than the normal content Wa, e.g., a piece of metal is present in the wrapping Wb of the package W1, furthermore, the foreign body in the first image data 27 can be fetched and recognized as data different in density from the content Wa. At the judgment section 31, therefore, it is possible to determine the position and size of the foreign body. In the inspection system 1, accordingly, the positional relationship between the content Wa and the wrapping Wb can be determined and the presence of the foreign body can also be detected by using the first image data 27 and the second image data 28.

In the inspection system 1, the X-ray detection image-taking line L1 passes through the gap 6c between the upstream conveyor mechanism 6a and the downstream conveyor mechanism 6b. Therefore, a scratch on the conveyor belt of the conveyor mechanism 6 or a foreign body attached to the conveyor belt can be prevented from being captured in the first image data 27, so that the image of the scratch or foreign body will never be erroneously identified as a foreign body enclosed in the package W1.

It should be noted that even if the light-shield member 43 or the cover member 44 has a scratch or a foreign body attached thereto, they appear as noise data always at the same position in the first image data 27 or the second image data 28, and the noise data can be removed by data correction at the image synthesis section 32 or the judgment section 31, so that they hardly cause detection errors.

Moreover, since the light detection image-taking line L2 passes through the gap 6c, the near infrared light or the like emitted from the illumination part 16 can be applied to the package W1 and the light having passed the package W1 can be detected by the optical sensor 15 to generate the second image data 28. Through the use of the transmitted light, the second image data 28 can be generated with the outline of the wrapping Wb of the package W1 detected clearly and accurately.

In the inspection system 1, the display switching section 35 can be operable to switch by operating one of the operation buttons on the display panel. By this switching, the image only of the first image data 27 or the image only of the second image data 28 can be displayed on the display screen of the display unit 19. Particularly, the image only of the second image data 28 based on the transmitted light from the illumination part 16 can be displayed, whereby when the wrapping Wb is formed of a light transmissive packaging material, whether or not the content is caught in the seal can be determined by obtaining the optical image of the package W1.

In the inspection system 1, accordingly, the image to be chosen may be replaced depending on the type of the wrapping Wb. For example, when the wrapping Wb is a bag that cannot be optically seen through, whether or not the content is caught in the seal or the foreign body is present can be determined by acquiring both the first image data 27 and the second image data 28 and displaying the combined image; when the wrapping Wb is formed of a light transmissive packaging material, whether or not the content is caught in the seal or the foreign body is present can be determined from the optical image by acquiring only the second image data 28.

When only the second image data 28 are acquired and only the optical image is used to determine whether or not something is caught or the foreign body is present, if near infrared light is used as the illumination light emitted from the illumination part 16, the illumination light can easily be transmitted through the packaging material, even though the wrapping Wb is formed of a patterned packaging material. On the other hand, if blue light is used as the illumination light, the difference in brightness between the wrapping Wb and the content Wa can be increased in the optical image to have a sharp contrast between the wrapping Wb and the content Wa.

Hereinbelow, other embodiments of the inspection system will be described with reference to FIGS. 5 to 7. In the following, the components different from those in the inspection system 1 according to the first embodiment will be mainly described. On the other hand, the components similar to those in the inspection system 1 according to the first embodiment will be denoted by the same reference signs, and detailed description will be omitted.

Figure 5:
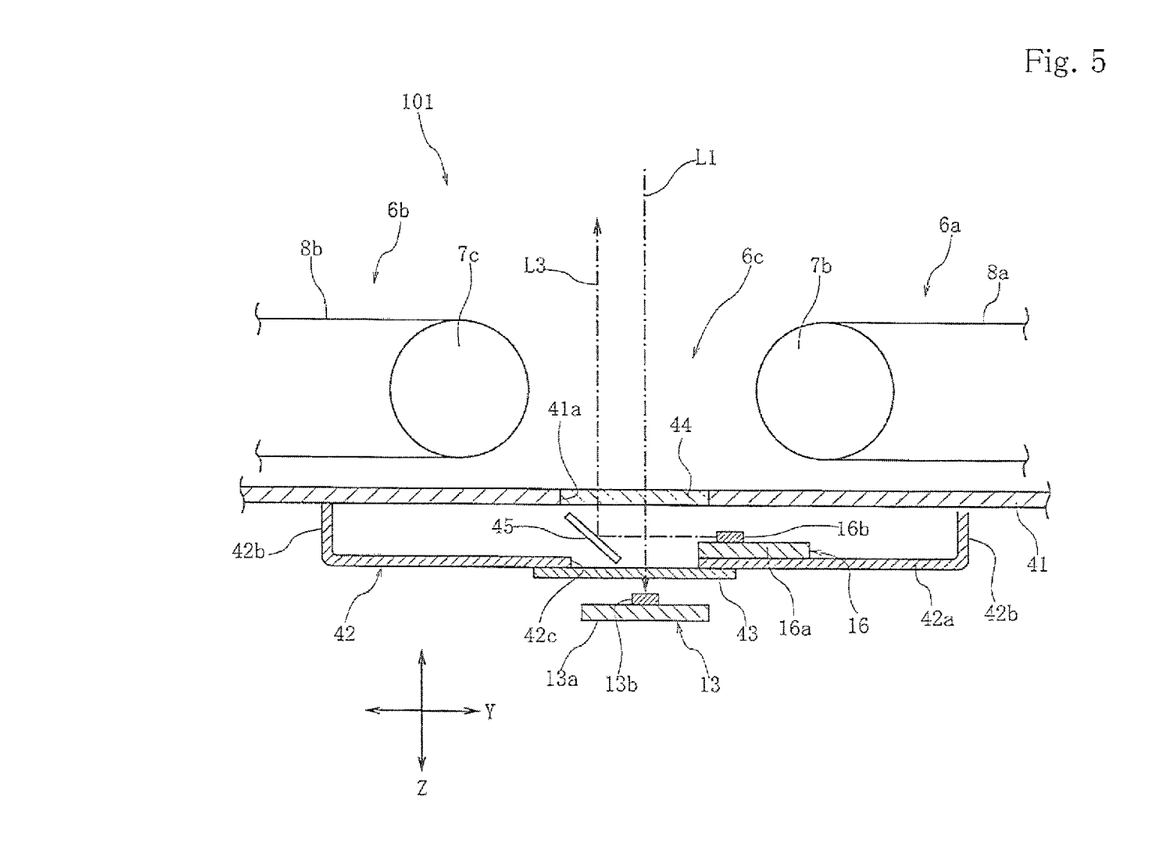
FIG. 5 A sectional view showing the arrangement of an illumination part and an electromagnetic-wave detection part in a package inspection system according to a second embodiment.

FIG. 5 shows an inspection system 101 according to a second embodiment, in which the partition 42 is provided below the floor plate 41 and the illumination part 16 is located within the region defined by the partition 42, as in the inspection system 101 shown in FIG. 3. From the light-emitting element 16b of the illumination part 16, the illumination light is emitted in the Y direction. Inside the partition 42, a lower reflection member 45 is provided to face the light-emitting element 16b such that the illumination light can be reflected upward by the lower reflection member 45, thereby providing the light detection image-taking line L3. Through the gap 6c, the light detection image-taking line L3 and the X-ray detection image-taking line L1 extend parallel to each other in the Z direction. The lower reflection member 45 is placed so as not to cross the X-ray detection image-taking line L1, whereby the lower reflection member 17 is prevented from being irradiated with strong X rays.

Also in the inspection system 101 according to the second embodiment, as in FIG. 2, the reflection member 17 is provided above the conveyor mechanism 6 such that the illumination light after passing through the gap 6c upward can be reflected in the Y direction and detected by the optical sensor 15. Also, the detection window 42c of the partition 42 is closed with the light-shielding member 43, while the opening 41a of the floor plate 41 is closed with the cover member 44.

Figure 6:
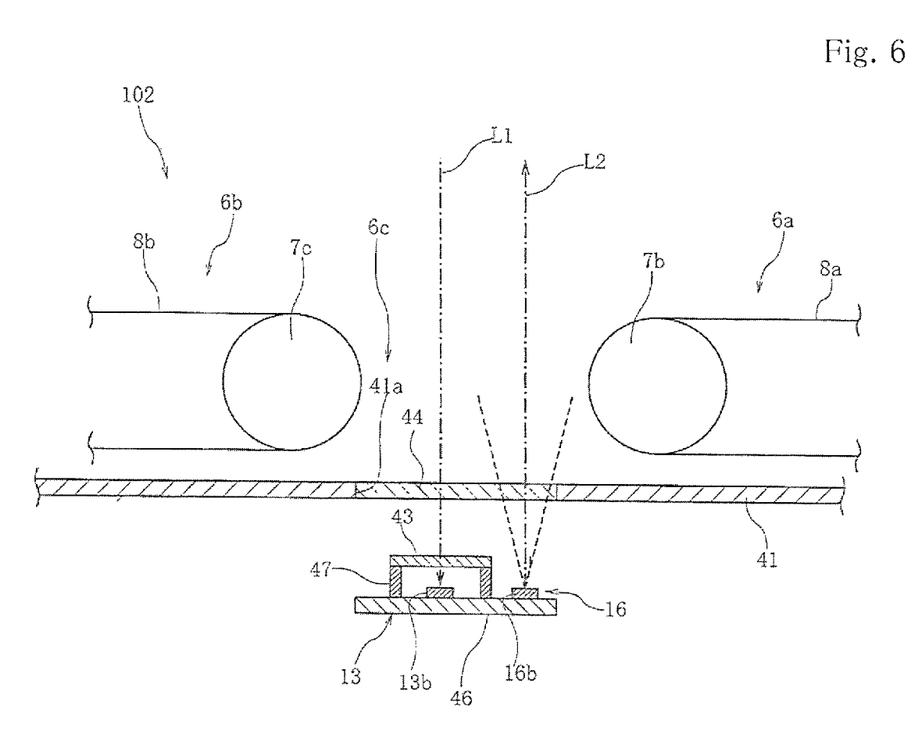
FIG. 6 A sectional view showing the arrangement of an illumination part and an electromagnetic-wave detection part in a package inspection system according to a third embodiment.

FIG. 6 shows an inspection system 102 according to a third embodiment, in which a common substrate 46 is fixed below the floor plate 41. A plurality of the X-ray detection elements 13b constituting the X-ray sensor 13 that is a line sensor are arranged on the common substrate 46, and a plurality of the light-emitting elements 16b constituting the illumination part 16 are also arranged on the common substrate 46.

On the common substrate 46, a partition 47 for separating the X-ray sensor 13 and the illumination part 16 is mounted with the upper opening of the partition 47 closed with the light-shielding member 43. Also in the inspection system 102, the illumination light emitted from the illumination part 16 can hardly be detected by the X-ray sensor 13.

Figure 7:
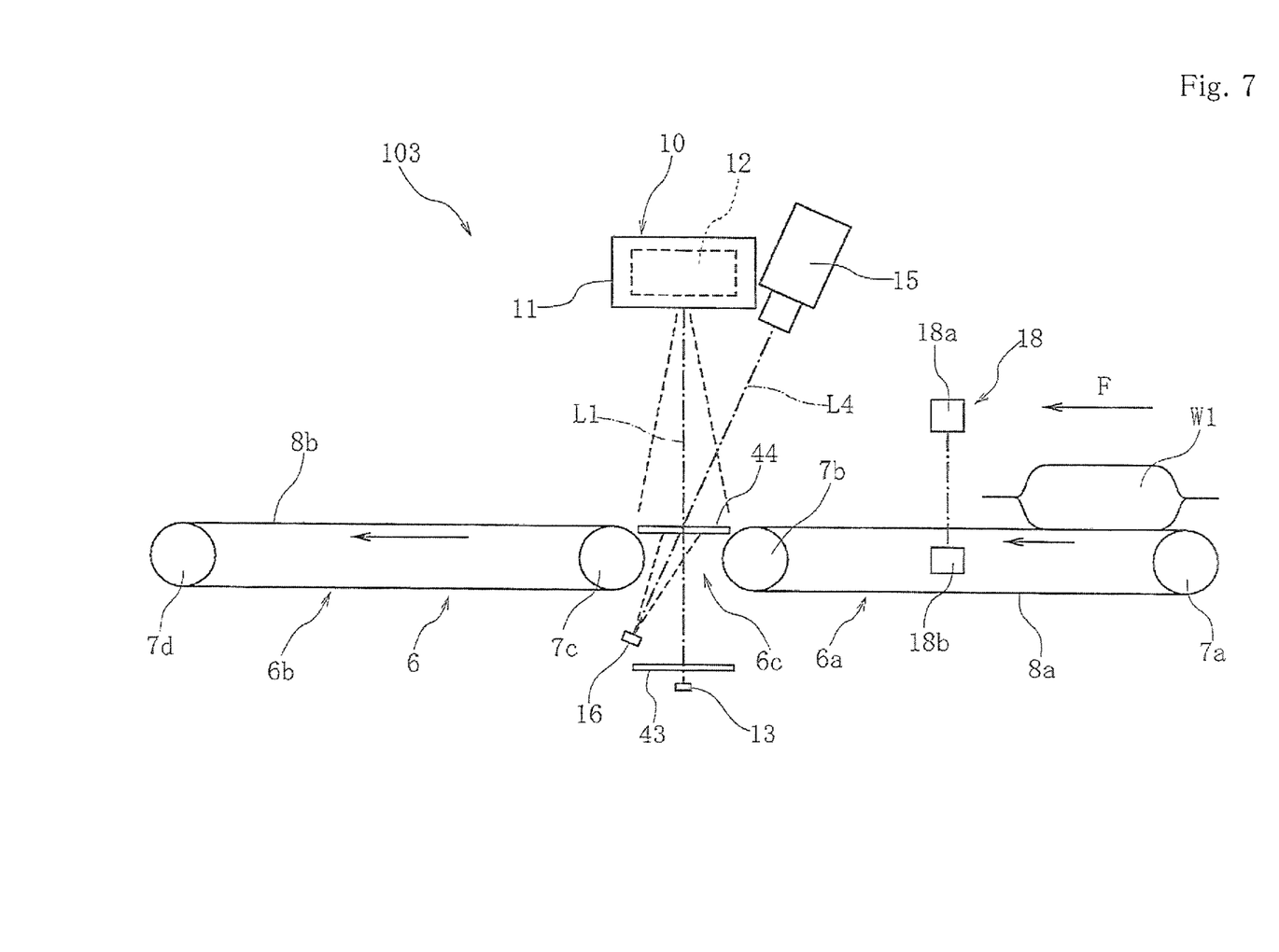
FIG. 7 A front view showing the internal construction of a package inspection system according to a fourth embodiment.

FIG. 7 shows an inspection system 103 according to a fourth embodiment, in which the X-ray sensor 13 and the illumination part 16 are placed below the conveyor mechanism 6. Although not illustrated in FIG. 7, the X-ray sensor 13 and the illumination part 16 are separated from each other by the partition such that the illumination light from the illumination part 16 does not directly enter the X-ray sensor 13. Moreover, the X-ray sensor 13 is covered with the light-shielding member 43.

The image-taking line L1 for detection of the X rays from the X-ray generator 10 passes through the gaps 6c and extends in the Z direction, while the light detection image-taking line L4 for imaging taking at the optical sensor 15 passes through the gap 6c but crosses the X-ray detection image-taking line L1.

The cover member 44 is placed at the gap 6c. The surface of the cover member 44 lies almost in the same plane as the upper surface of the conveyor belt 8a of the upstream conveyor mechanism 6a and the upper surface of the conveyor belt 8b of the downstream conveyor mechanism 6b. The package W1 conveyed in the Y direction by the upstream conveyor mechanism 6a can be passed to the downstream conveyor mechanism 6b such that it slides on the surface of the cover member 44.

The X-ray detection image-taking line L1 and the light detection image-taking line L4 cross each other in the vicinity of the surface of the cover member 44.

It should be noted that, although in the foregoing embodiments, the illumination part 16 and the X-ray sensor 13 are located at one side of the conveyance path of the package W, the present invention is not limited to such embodiments; the illumination part 16 and the X-ray sensor 13 may be located at opposite sides of the conveyance path of the package W. Also in this case, the noise superposition on the X-ray sensor due to the illumination light can be suppressed by providing the partition so as to prevent the illumination light from entering the X-ray sensor 13 and providing this partition with the light-shielding member 44.

According to the present invention, therefore, when both the illumination part 16 and the X-ray sensor 13 are placed in the X-ray or terahertz-wave shielding zone, i.e., the inspection zone for the package W, separated from the outside by the X-ray shielding sheet 5, as shown in FIG. 1, the noise superposition on the X-ray sensor due to the illumination light can be suppressed.

The above-mentioned X-ray or terahertz-wave shielding zone, i.e., the inspection zone for the package W is not limited to the one separated from the outside by the X-ray shielding sheet 5; for example, it may be a closed zone enclosed with partitions, wherein the conveyance surface of the conveyor belt is almost trapezoidal with the detection parts such as the X-ray sensor 13 and the optical sensor located at an upper conveyance path of the conveyor belt and with the partitions facing downward ascending and descending parts of the conveyor belt.

REFERENCE SIGNS LIST 1, 101, 102, 103 Inspection System
2 Package Conveyance Zone
6 Conveyor Mechanism
6a Upstream Conveyor Mechanism
6b Downstream Conveyor Mechanism
6c Gap
10 X-ray Generator (Irradiation Part)
13 X-ray Sensor (Electromagnetic-wave Detection part)
13a Sensor Substrate
13b X-ray Detection Element
15 Optical Sensor (Optical Detection Part)
16 Illumination Part
16a Illumination Substrate
16b Light-emitting Element
18 Position Sensor
19 Display Unit
20 Controller
24 First Image Data Generating Section
26 Second Image Data Generating Section
31 Judgment Section
32 Image Synthesis Section
41 Floor Plate
42 Partition
43 Light-shielding Member
44 Cover Member
47 Partition
W1 Package
Wa Content
Wb Wrapping

The invention claimed is:

1. A package inspection system comprising:
   a conveyor mechanism for conveying a package having a content in a wrapping;
   an irradiation part for irradiating the package with an X ray or a terahertz wave;
   an electromagnetic-wave detection part for detecting the X ray or terahertz wave transmitted through the package;
   an illumination part for illuminating the package with light; and
   an optical detection part for taking an optical image of the package, a partition being provided between the electromagnetic-wave detection part and the illumination part, the partition having a light-shielding member configured to allow passage of the X ray or terahertz wave but block or reduce light emitted from the illumination part, at least in a path through which the X ray or terahertz wave enter the electromagnetic-wave detection part,
   wherein the irradiation part and the optical detection part are provided at one side of a conveyance path of the package, and the illumination part and the electromagnetic-wave detection part are provided at another side thereof.

2. The package inspection system according to claim 1, wherein the illumination part is enclosed by the partition, the electromagnetic-wave detection part is provided outside the partition, and the partition is provided with the light-shielding member at a position facing the electromagnetic-wave detection part.

3. The package inspection system according to claim 1, wherein the electromagnetic-wave detection part is enclosed by the partition, the illumination part is provided outside the partition, and the partition is provided with the light-shielding member at a position facing the electromagnetic-wave detection part.

4. The package inspection system according to claim 1, wherein the light-shielding member contains carbon.

5. The package inspection system according to claim 4, wherein the light-shielding member is a carbon sheet containing carbon fibers and a binder resin.

6. The package inspection system according to claim 1, wherein the light-shielding member is formed of a PEEK (polyether ether ketone) resin.

7. The package inspection system according to claim 1, wherein a cover member configured to allow passage of the X ray or terahertz wave and the light emitted from the illumination part is provided between a conveyance path of the package and the electromagnetic-wave detection part and the illumination part.

8. The package inspection system according to claim 7, wherein the cover member is formed of a thermoplastic polyetherimide resin.

9. The package inspection system according to claim 1, wherein the conveyor mechanism has a gap through which the light emitted from the illumination part and the X ray or terahertz wave is allowed to pass.

* * * * *